United States Patent [19]

Thornton et al.

[11] Patent Number: 5,147,281
[45] Date of Patent: Sep. 15, 1992

[54] BIOLOGICAL FLUID PUMPING MEANS AND METHOD

[75] Inventors: Kenneth O. Thornton, Polk City; Steven J. Phillips, Des Moines, both of Iowa

[73] Assignee: Advanced Medical Systems, Inc., Polk City, Iowa

[21] Appl. No.: 512,944

[22] Filed: Apr. 23, 1990

[51] Int. Cl.$^5$ ............................................. A61M 1/10
[52] U.S. Cl. ........................................... 600/16
[58] Field of Search .......................... 600/16–18; 128/DIG. 3, 12; 604/7–10; 417/234, 415–417

[56] References Cited

U.S. PATENT DOCUMENTS

| | | | |
|---|---|---|---|
| 2,925,814 | 2/1960 | Vibber et al. | 417/417 |
| 3,433,983 | 4/1969 | Keistman et al. | 600/16 |
| 3,610,782 | 10/1971 | McGuire, III | 417/415 |
| 3,855,995 | 12/1974 | Bentley | 600/416 |
| 4,014,318 | 3/1977 | Dockcum et al. | 600/16 |
| 4,210,409 | 7/1980 | Child | 417/417 |
| 4,334,180 | 6/1982 | Bramm et al. | 600/17 |
| 4,610,658 | 9/1986 | Buchwald et al. | 604/9 |
| 4,824,337 | 4/1989 | Lindner et al. | 417/417 |

OTHER PUBLICATIONS

Page 282, paragraph 44, "The Vibrating Electromagnetic (VEM) Pump for a Totally Implantable Artificial Heart", S. Nitta et al.
1 page drawing (appears to be from a Japanese publication No. 3-19400 (FIGS. 1 and 2).
GRI Standard Pump Catalog, pp. 26 and 27; Gorman-Rupp Industries, Copyright Gorman-Rupp Ind., 1989.

Primary Examiner—William E. Kamm
Attorney, Agent, or Firm—Zarley, McKee, Thomte, Voorhees & Sease

[57] ABSTRACT

A ventricular assist device for temporary assistance to persons with failing or damaged hearts. A container includes inlet and outlet ports to the patient's circulatory system and a pumping component. It can also include a power source, and control elements, as well as other ventricular assist components. The pumping component operates off of a power supply, consumes a low amount of power, produces good pumping efficiency, and circulates the blood in an advantageous flow pattern with minimal trauma to the blood. The pumping device utilizes a moveable tubular member in which is positioned a one-way valve. The tubular moveable member is put in fluid communication with the flow path from inlet to outlet ports of the pumping component. The tubular member is reciprocatable by, for example, a solenoid and a return spring. Pumping of the blood is accomplished by the one-way valve opening to allow a volume of blood to pass from the inlet to outlet side of the valve when the tubular members traveling towards the inlet port, and then closing to push the blood out the outlet port when the tubular member is moving in the opposite direction. A one-way flow restriction device can replace the valve.

26 Claims, 3 Drawing Sheets

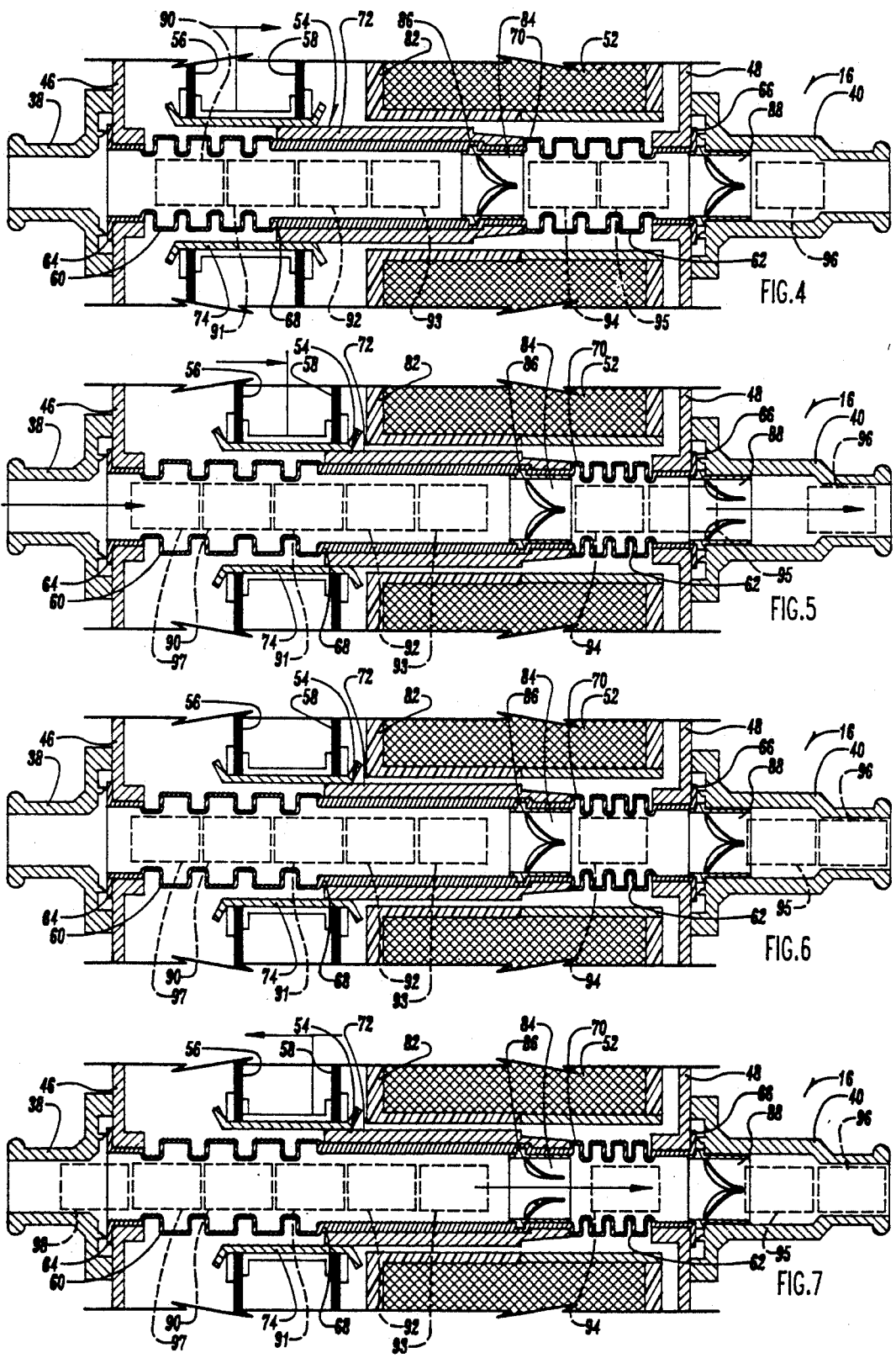

BIOLOGICAL FLUID PUMPING MEANS AND METHOD

SUMMARY OF THE INVENTION

A. Field of the Invention

The present invention relates to ventricular assist devices, and in particular, to a small, low power ventricular assist system. It uses a pumping means which is reliable, efficient, and minimizes damage to blood cells.

B. Problems in the Art

Heart attack victims many times require mechanical assistance to aid and stabilize the heart and patient in order to maintain blood circulation for a temporary period until the patient can be moved to a hospital where more appropriate equipment exists. This need is particularly acute when the victims are located at long distances from heart treatment hospitals, such as in outlying or remote areas from major towns and cities. There is simply a need for a better ventricular assist system whether at a remote location, or at a completely equipped hospital.

Mechanical circulation of blood is by what is commonly called ventricular assistance. Conventionally, this is accomplished by utilizing peristaltic, centrifugal, diaphragm, or balloon pumps. Peristaltic pumps utilize mechanical compression action to create a mechanical pumping circuit. Centrifugal pumps use rotary movement to throw the fluid. Diaphragm pumps move a diaphragm against the pumped fluid.

These pumps are connected into the patient's circulatory system utilizing a cannula and tubing. Normally, the cannula are inserted by medical personnel into a major artery and vein. Tubing is then used to connect the cannulas and the assist pump.

Conventional pumps are in wide spread use, but do have certain problems and deficiencies. There is therefore a real need in the art for a ventricular assist device which improves over conventional systems, in particular with regard to size, complexity, damage to blood cells and mechanical and fluid-flow reliability.

One problem of pumps (with current assist devices) is that they require significant amounts of power; generally electrical power. Many require several conversions of power. A peristaltic pump needs to use electricity to a compressor to pneumatically drive mechanical rollers which squeeze or compress a flexible tubing to move the blood. Most devices are also comparatively large and bulky which is disadvantageous for treatment of patients in remote areas and in emergency vehicles.

An example of specific problems with conventional pumps is illustrated with respect to peristaltic pumps. The compressive action of peristaltic pumps is noisy and inefficient. Significantly, the compressive action is very turbulent and traumatic on the blood and may cause significant cell damage. As is known in the art, the trauma to the blood can be measured by a hemolytic index. In the case of peristaltic pumps (which generally have the best rating for hemolytic index for conventional pumps), the hemolytic effect is quite high.

The result of these problems and deficiencies is that conventional pumps simply do not make easily portable ventricular assist systems and thus are somewhat difficult to use as instruments for such critical, emergency work. Still further, their hemolytic affect on the blood is such that it cuts down on the amount of time a patient can be hooked up to such devices so that they have deficiencies, even when used in the hospital.

As can be seen from the above discussion in the context of the critical environment of care for such debilitated patients, the need for care improvement options is significant.

It is therefore a principal object of the present invention to provide a biological fluid pumping means and method which solves or overcomes many problems and deficiencies in the art of conventional systems such as peristaltic, centrifugal, diaphragm, and balloon systems.

A further object of the invention is to provide a means and method as above described which can be portable, easily usable, quiet in operation and low in power consumption.

A still further object of the invention is to provide a means and method as above described which can use a portable, self-contained power supply which can accomplish the assist pumping for several hours at a remote location, or can be used as a ventricular assist device at a hospital.

Another object of the present invention is to provide a means and method as above described which maintains pumping efficiency in its complete range of flow and for many different through-puts and pumping speeds.

A still further object of the invention is to provide a means and method as above described which consumes a minimum amount of power yet maintains its pumping efficiency through its range of flow and operation.

Another object of the present invention is to provide a means and method as above described which maintains a laminar flow of blood to reduce turbulence, clotting, hemolysis, and other problems during pumping and circulation.

Another object of the present invention is to provide a means and method as above described which is gentle and less traumatic on the whole blood cells as it is being used and improves the hemolytic index rating for the blood, as opposed to other types of pumps or systems.

These and other objects and advantages of the present invention will become more apparent with reference to the accompanying drawings, specification and claims.

SUMMARY OF THE INVENTION

The invention comprises a means and method of improved ventricular assistance. It can be self-powered in a portable housing containing a pump for the blood as well as other elements utilized in ventricular assistance. It also can include control components and circuits to vary the pumping and ventricular assistance process according to need or desire. Connections are included for inserting the ventricular assist device into a circulation loop for the patient by utilizing appropriate tubing and cannula.

Reduction of size of the system is allowed in part by the use of an accelerative solenoid means in modified form as the pump mechanism. The solenoid basically pumps blood by reciprocating a moveable tubular member in the flow path according to successive energization of a magnetic field, generally by an electrical coil which attracts a magnetized portion on the moveable tube. This creates accelerative and inertial flow. A flow restrictor, for example a one-way valve, is positioned inside the moveable tube. When the tube moves towards the inlet port, the valve opens momentarily to let blood pass (or lessens restriction on flow). When the tubular member reciprocates towards the outlet port the one-way valve closes momentarily and pushes blood out the port, while at the same time drawing in additional blood. The movement of the blood is therefore acceleratory and inertial in the sense that it is continuously being pushed (accelerated) and drawn (inertial movement) with the high speed reciprocation of the tubular member and one-way flow restrictor. It is also gentle on the blood in that the amount of time blood actually comes into abutment with the valve or restrictor is short and transient, and the entire way in which the blood is transported is non-turbulent, gentle, and produces a laminar flow of blood reducing blood cell damage and hemolysis.

The invention can also include a second one-way valve (or a flow restrictor of some type) which is on the outlet port side of the first one-way valve or restrictor but held stationary. It opens and closes in the same direction as, but at different times from, the first one-way valve or restrictor. It also serves to prevent backflow or reflux of blood back into the pump, making the pumping action smoother.

By nature of its operation, a solenoid is low power, quiet, and efficient; even over the range of flow for the device.

BRIEF DESCRIPTION OF THE DRAWINGS

FIGS. 4, 5, 6 and 7 each shows an identical isolated portion of FIG. 3 but depicts different stages of the pumping action of the pump of FIG. 2.

DETAILED DESCRIPTION OF THE PREFERRED EMBODIMENT

Figure 1:
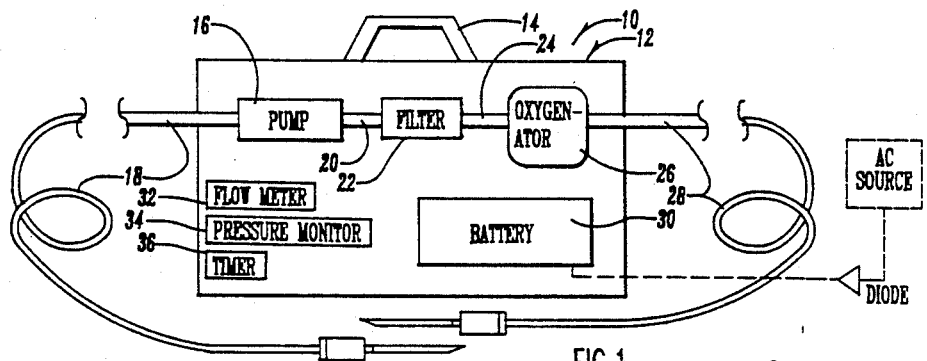
FIG. 1 is a schematic view of a ventricular assist system according to the present invention.

In order to gain a better understanding of the invention, a detailed description of a preferred embodiment of the invention will now be described with reference to the drawings. Reference numerals are used in the drawings to indicate specific parts or locations. The same reference numerals will be used to indicate the same parts or locations in all the drawings throughout this description unless otherwise indicated.

With particular reference to FIG. 1, a ventricular assist device 10 is schematically depicted. It all fits in a briefcase-sized housing 12, which can have a handle 14 for portability by one person. It contains all the working elements of device 10. A pump 16 is connectable to an inlet conduit 18. In this preferred embodiment, the output of pump 16 is connected via conduit 20 to an arterial filter 22 (available from Medtronics), which is in turn connected by conduit 24 to oxygenator 26 (Maxima oxygenator from Medtronics). Oxygenator 26 is then connectable to outlet conduit 28. It is to be understood that the present invention can also be used advantageously as a replacement for conventional ventricular devices in hospitals, and does not have to be portable or necessarily contained in a briefcase like housing. Further, the system may work well without arterial filter 22 and/or oxygenator 26. In many cases, pump 16 can pump blood to get sufficient perfusion (and oxygenation) through the patient's lungs.

A ventricular assist device 10, as is well known in the art, serves to assist circulation and oxygenation of blood for a patient whose heart has fully or partially failed. The inlet and outlet conduits 18 and 28 are connectable into a patient's circulatory system by means known within the art. Generally this entails cannula (available, for example, from Datascope, N.J., or Biomedicus, Eden Prairie, Minn.) attached to conduits 18 and 28 which in turn are inserted into a major vein and artery (such as femoral vein and artery), respectively.

FIG. 1 also shows that the portable housing 12 can contain a power source in the form of an electric battery 30. Generally, battery 30 is rechargeable and can power the components of device 10 for several hours, at a minimum. Battery 30 provides voltage at around 60 hertz. If alternating current (115 V, 50/60 hz) is used, a diode can convert the AC to DC impulses.

Still further, housing 12 can contain such things as a flow meter 32, pressure monitor 34, and timer 36. All of which are available from a variety of vendors and can be integrated into device 10 according to known principles and via use of known connections.

Device 10 therefore represents an advantageous consolidation of elements needed for ventricular assistance in one portable self-powered package. It can therefore easily be transported in emergency vehicles and hand carried to the patient, even in a remote or outlying area from a vehicle. It can also be used at a location that does not have readily available access to electrical power. Alternatively, it can be used in place of a conventional ventricular device in a hospital or at any location.

Figure 2:
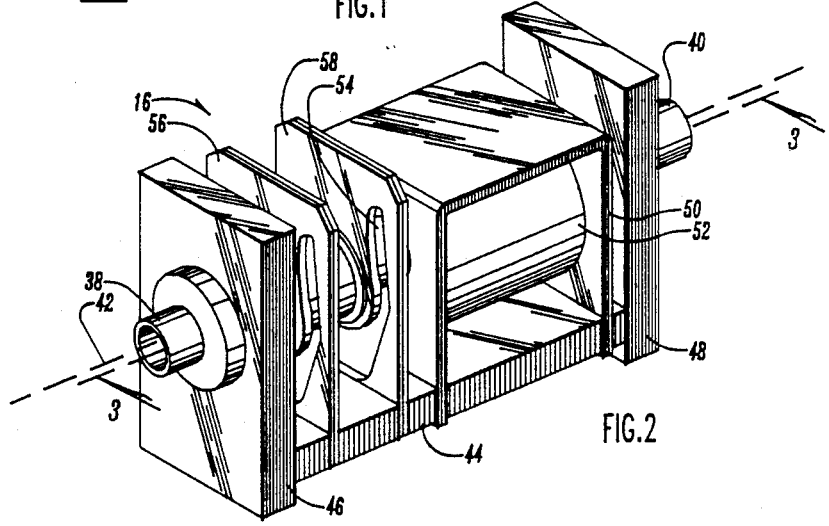
FIG. 2 is a schematic view of a pump used in FIG. 1.

FIG. 2 shows in isolated perspective the preferred embodiment of pump 16. Inlet and outlet ports 38 and 40 are positioned along linear axis 42 which defines the flow path through pump 16. A base 44 is rigidly secured to end plates 46 and 48. Bracket 50 is in turn rigidly secured to base 44. A cylindrical coil 52 is attached to bracket 50 and includes a cavity disposed along linear axis 42.

A tubular element 54 is also positioned along linear axis 42 and extends into the cavity through coil 52 at one end, and has a second end which extends through and is secured in upright sets of leaf springs 56 and 58.

It is to be understood that a flow path of blood through pump 16 begins with inlet port 38, travels through a flexible, enlargeable connection portion 60 (see FIG. 3) between inlet port 38 and one end of tubular element 54, then through tubular element 54, then through a flexible, enlargeable connection portion 62 (see FIG. 3) between tubular element 54 and outlet port 40, and then out through outlet port 40.

Tubular element 54 is reciprocateable along linear axis 42 for a defined distance. It reciprocates in response to energization and de-energization of coil 52 which attracts a magnetic portion connected to tubular element 54. It moves forward against leaf springs 56 which then resiliently returns tubular element 54 back towards a resting position upon de-energization of coil 52. This reciprocation pumps fluid through pump 10.

Figure 3:
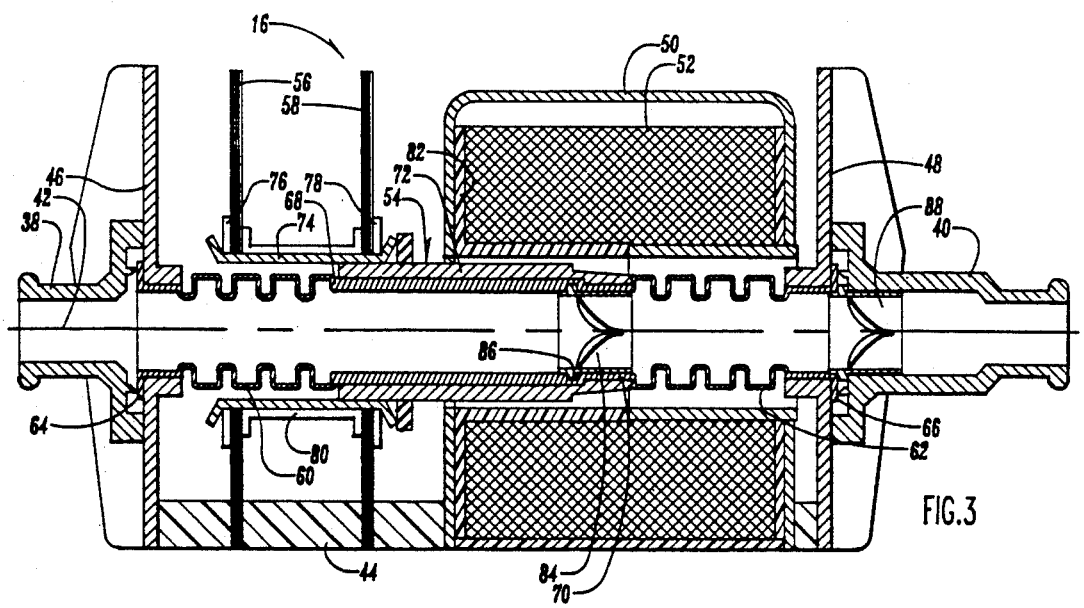
FIG. 3 is a sectional view taken along line 3—3 of FIG. 2.
Figure 8:
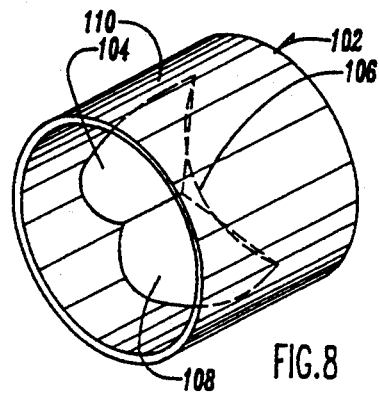
FIG. 8 is a perspective view of a one-way valve which can be used in the pump of FIG. 2.

FIG. 3 is a sectional view showing the internal components of pump 16. Connection portions 60 and 62 are flexible and expandable segmented sleeves that are clamped in position at outer ends 64 and 66 between end plates 46, 48 and inlet and outlet ports 38 and 40, respectively. In the preferred embodiment connection portions 60 and 62 are made of a bio-compatible silicone elastic material marketed under the trademark Silastic ™ from Dow-Corning. At inner ends 68 and 70, connection portions 60 and 62 can be connected to the tubular element 54, but in the preferred embodiment, the Silastic ™ material comprises both the connection portions 60 and 62, as well as tubular element 54. These three portions can therefore be made as one piece to eliminate joints and to ensure blood pumped through pump 10 contacts only biocompatible material. The flow channel through pump 16 is therefore substantially linear, continuous, and sealed. Additionally, the flexible connection portions 60 and 62 allow tubular element 54 to move along linear axis 42, while maintaining the sealed fluid pathway.

FIG. 3 also shows how tubular element 54 is sheathed with, at least in part, and attached to a magnetic metal mass or material 72. Material 72 is of such configuration that it is pulled by a magnetic field created by coil 52, when energized, in a right-hand direction in FIG. 3. It is to be understood that material 72 is clamped by a spool 74 which in turn passes through apertures in both sets of leaf springs 56 and 58. Washers 76 and 78, along with a spacer 80, hold leaf springs 56 and 58 in the position shown in FIG. 3 with respect to spool 74. Thus, upon movement of tubular element 54, leaf springs 56 and 58 are moved out of their normal position and attempt to restore tubular element 54 to its original resting position.

It is to be understood that an insulating shield 82 can be positioned around the left-hand most interior portion and end of coil 52. Coil 52 produces the strongest field and pulling attraction to metal material 72 at its right-hand-most portion as seen in FIG. 3. This controls how far tubular element 54 can be pulled along axis 42.

Tubular element 54 includes one-way valve 84, which is locked into place in annular groove 86 around the interior of tubular element 54 at its right-hand most end as shown in FIG. 3. One-way valve 84, as pictured, is a tri-leaf Kolff or Utah valve and is shown in a closed position.

The preferred embodiment also includes a second one-way valve 88 which is secured in place in outlet port 40. It is therefore to be understood that upon reciprocation of tubular element 54, one-way valve 84 is translated towards and away from the stationary second one-way valve 88.

FIGS. 4, 5, 6 and 7 depict how pump 16 accomplishes pumping action of blood. Each of these Figures shows the portion of pump 16, in cross section such as FIG. 3, along the linear axis 42.

FIG. 4 depicts pump 16 in what will be called its resting position. Dashed line boxes 90-95 schematically represent approximate equivalent volumes of blood in the blood flow path. As can be seen in FIG. 4, both valves 84 and 88 are closed and coil 52 is not energized. However, upon beginning energization of coil 52, tubular element 54 would begin to be pulled in a right-hand direction (indicated by arrow) in FIG. 4. The pressure on the outlet side of valves 84 and 88 would cause them to remain closed.

As tubular element 54 continues to move right, it would shorten the distance between valves 84 and 88, and elongate the distance between valve 84 and inlet port 38. Blood blocks 94 and 95 would then be pushed, accelerated, and slightly compressed and the fluid pressure would open valve 88 and push that blood out of outlet port 40 while at the same time drawing in additional blood blocks such as 97 at the inlet port 38 side (see FIG. 5).

When tubular element 54 reaches its maximum right-hand most position (such as shown in FIG. 6) and forces blood block 95 through valve 88, upon release of fluid pressure on the inlet side of valve 88, valve 88 would again close. Then, when coil 52 is de-energized, leaf springs 56 and 58 will bring tubular element 54 back in a left-hand direction (FIG. 7) which will increase the distance and volume of space between valves 84 and 88, causing the blood blocks 93, 92, etc. to exert enough fluid pressure on valve 84 to open valve 84 and fill into element 54. It should be noted that valve 88 remains closed. This stops any reflux or backflow of blood that has already passed through valve 88 and contributes to a smoother continuous, less turbulent pumping action.

Tubular element 54 generally reciprocates back and forth at around 60 hertz. In the preferred embodiment, pump 16 is basically self-priming and can pump up to 4.5 liters per minute of blood. The pumping action is acceleratory and inertial in the sense that as the circulation is started, tubular element 54 moves in the left-hand direction in the drawings with minimum resistance actually over the blood that is flowing in a right-hand direction, and then gets a push from and is accelerated by valve 84 when tubular element 54 is pulled back in a right-hand direction. As tubular element 54 moves towards the inlet end of pump 10, it captures incoming blood which is moving oppositely by inertia. The valve or valves then hold the blood in element 54 when it changes direction and moves towards the outlet end and maintains the inertia of the blood, but with a minimum of contact or disruption of the blood.

The configuration of pump 16 also imposes a minimum of pressure or turbulence on the blood. The contact of blood onto the pushing surfaces is minimal and transient, and the very rapid reciprocation maintains the blood in what is known as a laminar flow where the blood flows in distinct linear layers without turbulence, thrashing and sidewall impact. A minimum number of joints or protrusions exist along the flow path. All of these factors contribute to a smooth, reliable, and improved blood flow with less pooling, clotting, or damage. Thus significant improvements in the level of hemolysis are achieved. The invention provides on the order of a two-fold improvement in hemolytic index over the next best type of pump, the peristaltic pump.

Pump 10 also maintains high pumping efficiency in the sense that its efficiency is the same whether it is pumping 0.02 liters/minute or 6 liters/minute.

Figure 9:
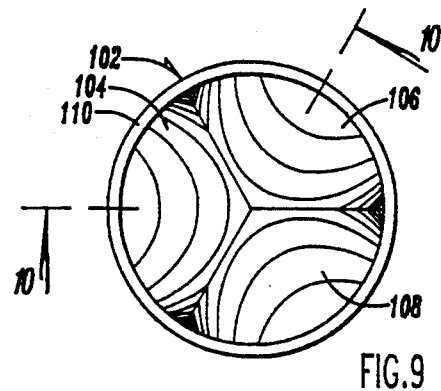
FIG. 9 is a front end view of the valve of FIG. 8.

FIGS. 8-11 depict the preferred embodiment for valves 84 and 88. It is preferred that the tri-leaf valve 102 of FIGS. 8-11 be utilized. This valve is known as a "Utah valve" or Kolff valve. It is a tri-leaflet polyurethane valve whereby each leaf 104, 106, 108 has a portion secured to the interior wall of annular casing 110. FIG. 9 shows valve 102 in its closed position. This can be compared with FIG. 11 which shows leafs 104, 106, 108 in an open position. The dashed lines represent the closed position.

Figure 10:
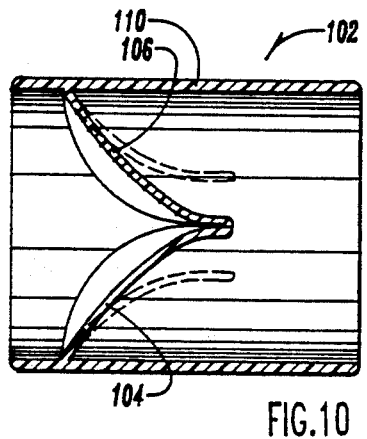
FIG. 10 is a sectional view taken along line 10—10 of FIG. 9.
Figure 11:
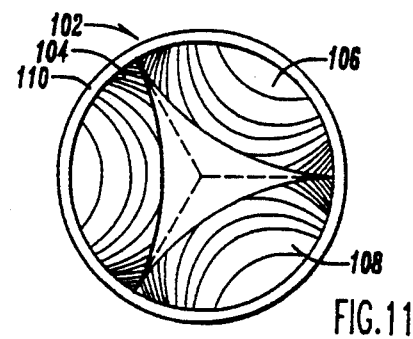
FIG. 11 is a front end view of the valve of FIG. 8 showing the valve in an opened position, with the closed position being indicated with broken lines.

FIG. 10 is a cross sectional view depicting in solid lines a closed position and in broken lines the open position. Valve 102 is preferred because it is more sensitive and reliable.

Coil 52 can be wound to directly handle pulsed direct current, and would not then need a power inverter. Battery 30 can comprise VDC or voltage (direct current), or combine a power inverter with VDC. Battery 30 can be rechargeable. In order to achieve improved operation of pump 16, the preferred embodiment can include a special winding for coil 52. A stellarator winding, as known in the art, could be utilized which increases the amount of pulling power of coil 52 with respect to magnetic metal material 72 on tubular sleeve 54. A first layer of wires is angularly wrapped around a core. A second layer of wires is perpendicularly wrapped to the linear axis 42. The special winding adds additional propensity of the magnetic field created by the coil to be directed in a desired direction. This impacts on the pulling power of coil 52 a stellerator winding configuration can be made to increase the amount of thrust of the tubular sleeve in a first direction and decrease the thrust in the opposite direction. The results are well known in the art as known to those of ordinary skill in the art.

Figure 12:
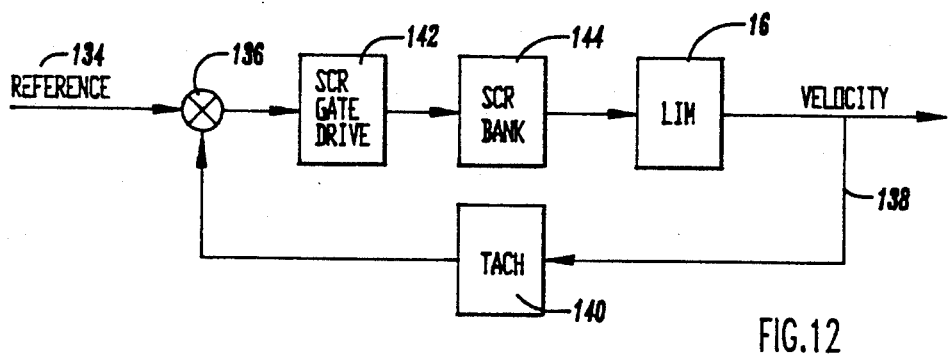
FIG. 12 is a schematic view of a control circuitry for the pump of FIG. 2.

FIG. 12 depicts a control circuit for controlling operation of the pump 16. A reference signal 34 set by a control level or knob is sent to comparator 136. The velocity of blood flow emanating from pump 16 is monitored, by a transducer such as is well known within the art, and a signal 138 is sent to tachometer 140. Tachometer 140 in turn sends a signal to comparator 136. The resulting error signal from comparator 136 is sent to SCR gate drive 142 and, depending on the type of error signal gate drive 142, instructs SCR bank 144 to either increase or decrease the frequency of operation of pump 16.

The included preferred embodiment is given by way of example only, and not by way of limitation to the invention, which is solely described by the claims herein. Variations apparent to one skilled in the art are intended to be included within the invention defined by the claims.

For example, the invention can also work with just one-way valve 84 in reciprocating tubular element 54. Second valve 88 is not needed, but does operate to stop back flush or back flow, as well as even out pressures along the pump.

It could also utilize one or more fluid flow restriction means, instead of one-way valves, which do not open and close in a sealing fashion, but present greater resistance to flow in one direction than another. An example would be a helically-shaped member which presents less flow restriction in a first direction than a second direction.

Alternative ways can be used to reciprocate the tubular member. For example, instead of one solenoid coil and a return spring, two solenoid coils could be used; one to push, one to pull the tubular member.

The device also can be used in a variety of ways. For example, when performing balloon angioplasty, a pump 16 could be connected into the cannula used for the procedure by a Y-connector. If pumping assist is needed, it would be immediately available. Presently, any heart stoppage would require immediate bypass surgery.

What is claimed is:

1. A biological fluid pumping means comprising:
   a bio-compatible tubular fluid conduit having a longitudinal axis, an inlet end, and an outlet end;
   a bio-compatible flow restriction means having an inlet side and an outlet side secured in the conduit, the flow restriction means resisting fluid flow from the outlet side to the inlet side;
   the conduit including a rigid tubular middle portion and expandable and contractible portions an opposite sides of the middle portion so that the middle portion can reciprocate a distance between the expandable and contractible portions;
   means immediately adjacent to the conduit for reciprocating the middle portion of the conduit generally along the longitudinal axis to produce flow of biological fluid through the conduit; and
   connecting means for putting a biological fluid into fluid communication with the inlet and outlet ends of the conduit.

2. The biological fluid pumping means of claim 1 wherein the conduit is made of a silicone-elastic material.

3. The biological fluid pumping means of claim 1 wherein the one-way flow restriction comprises a one-way valve.

4. The biological fluid pumping means of claim 3 wherein the one-way valve comprises a tri-leaf Kolff valve.

5. The biological fluid pumping means of claim 1 further comprising a second flow restriction means positioned stationarily with respect to but spaced apart from the flow restriction means generally at the outlet end of the conduit.

6. The biological fluid pumping means of claim 1 wherein the means for reciprocating the conduit comprises a magnetic mass secured to the conduit and means for producing a magnetic field for attracting the magnetic mass.

7. The biological fluid pumping means of claim 6 wherein the means for producing a magnetic field comprises an electric coil.

8. A portable means for pumping biological fluid comprising:
   a portable container means containing;
   a solenoid means including;
      a housing means having opposite open ends and a cavity between the opposite open ends;
      a tube means having a longitudinal axis, which is reciprocally movable in the cavity between a resting position and an opposite position along the longitudinal axis;
      a coil means for causing linear movement of the tube means from a resting position in a first direction through the cavity;
      a means for causing resilient linear movement of the tube means in a second direction opposite to the first direction through the cavity to bias the tube means to the resting position;
   the tube means comprising:
      a tubular member having opposite open ends;
      a magnetizable means surrounding at least a portion of the tubular member;
      a connection means between each opposite open end of the tubular member and stationary inlet and outlet conduits, the connection means being expandable and retractable during reciprocation of the tube means;
   movement of the tube means from the resting position in the first direction causing the one way flow resistance means to allow a volume of biological fluid to pass from inlet side to outlet side of the one way flow restriction means; and movement of the tube means in the second direction causing the one-way flow resistance means to move a volume of biological fluid on the outlet side of the one-way flow resistance means out of the outlet, to pump biological fluids so that reciprocation of the tube means in combination with the operation of the one-way flow resistance means causes accelerative and inertial flow of the fluid.

9. The portable means of claim 8 having a size comparable to a briefcase so that it can be carried by one person.

10. The portable means of claim 8 including an electrical power source means wherein electrical power is provided to the solenoid means by direct current impulses from a direct current impulse source connected to the electrical power source means.

11. The portable means of claim 10 including an alternating current source associated with the electrical power source means and a diode, wherein the direct current impulses are created by the diode which modifies an alternating current input from the alternating current source.

12. The portable means of claim 8 including supporting means to guide the tube means wherein the tube means follows a generally linear movement between stationary inlet and outlet conduits.

13. The portable means of claim 8 wherein the coil means is offset from the tube means along the first direction when the tube means is in the resting position.

14. The portable means of claim 8 wherein the means for causing resilient linear movement comprises at least one spring.

15. The portable means of claim 8 wherein the one-way flow resistance means comprises a one-way valve.

16. The portable means of claim 15 wherein the one-way valve comprises a Kolff tri-leaf valve.

17. The portable means of claim 8 wherein the connection means are made of a bio-compatible material.

18. The portable means of claim 8 further comprising a second one-way flow resistance means positioned within the stationary outlet conduit, the second one-way flow resistance means remaining closed upon movement of the impeller means in the first direction, and opening upon movement of the impeller means in the second direction.

19. A portable ventricular assist means for temporary maintenance of sufficient pumping of blood through a patient comprising:
 a portable carrying case;
 a pumping means inside the case, the pumping means including an inlet port and an outlet port for blood;
 connection means for putting tubing and cannula in fluid communication with the inlet port and outlet port;
 power means within the case for supplying electrical power to the pumping means;
 a tubular member having a longitudinal axis and which is linearly reciprocable along the axis;
 a magnetized piece attached to the tubular member;
 expandable tubular sleeves connected at first ends to opposite ends of the tubular member, and connected at second ends to stationary conduits which are in fluid communication with the inlet and outlet ports, the sleeves allowing linear reciprocation of the tubular member between the stationary conduits;
 one way valve means positioned within the tubular member;
 coil means positioned relative to the magnetized piece on the tubular member to draw the tubular member towards the inlet port and cause opening of the one-way valve means which electrically energized;
 bias means for restoring the tubular member to an original position and causing closing of the one-way valve means when the coil means is not electrically energized;
 the one way valve means reciprocating with the tubular member upon alternating periodic energization of the coil means to pump blood between the inlet and outlet ports.

20. The assist means of claim 19 further comprising cannula for insertion into the appropriate artery and vein in a patient, and corresponding conduits which are attachable to the inlet and outlet ports of the pumping means.

21. The assist means of claim 19 wherein the pumping means and coil means includes a solenoid means.

22. The assist means of claim 19 wherein the tubular sleeves are made of elastomeric material and are expandable and retractable.

23. The assist means of claim 22 wherein the tubular sleeves are made of a bio-compatible material.

24. The assist means of claim 19 wherein the bias means comprises a spring means.

25. A method of pumping biological fluid comprising:
 connecting first and second fluid conduits in fluid communication with a biological fluid;
 placing opposite ends a movable hollow tube having a one-way flow restriction means positioned therein in fluid communication with the first and second fluid conduits by connecting expandable and contractible tubular portions between opposite ends of the hollow tube and the first and second fluid conduits;
 reciprocating the hollow tube by reciprocation means which is immediately adjacent the hollow tube so that the hollow tube reciprocates between the expandable and contractible tubular positions; and
 controlling operation of the reciprocation means to cause desired reciprocation of the hollow tube to alternatingly move the tube in a first direction to cause the flow restriction means to allow a volume biological fluid through, and move the tube in a second direction to allow the flow restriction means to move a volume of biological fluid previously passing through the flow restriction means out of the tube, and draw an additional volume of biological fluid into the tube.

26. A method of ventricular assistance to a patient comprising:
 putting the patient's circulatory system in fluid communication with an inlet port and an outlet port;
 connecting a movable hollow fluid conduit between the inlet and outlet port by connecting expandable and contractible tubular portions between opposite ends of the hollow tube and the first and second fluid conduits;
 positioning a one-way flow restriction means in the movable hollow fluid conduit; and
 reciprocating the movable fluid conduit by a reciprocation means which is immediately adjacent to hollow tube so that the hollow tube reciprocates between the expandable and contractible tubular portions to alternatingly lessen flow restriction when moving towards the inlet port, and increase flow restriction when moving towards the outlet port, to capture succeeding volumes of blood and move the succeeding volumes of blood from the inlet to outlet ports.

* * * * *